(12) United States Patent
Wang et al.

(10) Patent No.: US 8,947,663 B2
(45) Date of Patent: Feb. 3, 2015

(54) DUAL-MODULATION FARADAY ROTATION SPECTROSCOPY

(71) Applicants: Yin Wang, Princeton, NJ (US); Gerard Wysocki, Princeton, NJ (US)

(72) Inventors: Yin Wang, Princeton, NJ (US); Gerard Wysocki, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 14/215,739

(22) Filed: Mar. 17, 2014

(65) Prior Publication Data

US 2014/0268148 A1   Sep. 18, 2014

Related U.S. Application Data

(60) Provisional application No. 61/787,651, filed on Mar. 15, 2013.

(51) Int. Cl.
*G01J 4/00* (2006.01)
*G01J 4/04* (2006.01)
*G01N 21/21* (2006.01)

(52) U.S. Cl.
CPC .. *G01J 4/04* (2013.01); *G01N 21/21* (2013.01)
USPC ......................................................... 356/364

(58) Field of Classification Search
USPC ............................... 356/364; 250/559.09, 225
See application file for complete search history.

(56) References Cited

U.S. PATENT DOCUMENTS

| 7,365,352 B2 * | 4/2008 | Muta et al. ..................... 250/573 |
| 7,405,826 B2 * | 7/2008 | Gibbs et al. ..................... 356/432 |
| 2006/0001876 A1 * | 1/2006 | Gibbs et al. ..................... 356/364 |
| 2006/0262311 A1 * | 11/2006 | Muta et al. ..................... 356/437 |

OTHER PUBLICATIONS

Lewicki, R., Doty, J. H., Curl, R. F., Tittel, F. K., and Wysocki, G., "Ultrasensitive detection of nitric oxide at 5.33 mu m by using external cavity quantum cascade laser-based Faraday rotation spectroscopy," Proceedings of the National Academy of Sciences of the United States of America, 106(31), 12587-12592 (2009).

Yin Wang, Michal Nikodem, Jake Hoyne and Gerard Wysocki, "Heterodyne-enhanced Faraday rotation spectrometer," Proc. SPIE 8268, 82682F, (Jan. 2012).

* cited by examiner

*Primary Examiner* — Roy M Punnoose
(74) *Attorney, Agent, or Firm* — Meagher Emanuel Laks Goldberg & Liao, LLP

(57) ABSTRACT

A dual-modulation Faraday rotation spectroscopic (FRS) system is disclosed. The FRS system uses an FRS sample cell configured to subject a sample to a low frequency modulated magnetic field. The system includes a polarized laser light source configured to generate a high frequency wavelength-modulated light beam incident on the sample, the high frequency wavelength-modulated light beam being modulated at a higher frequency than the low frequency modulated magnetic field. A polarizer is configured to receive from the sample a transmitted light beam having a modulated polarization having a polarization rotation and translate the modulated polarization of the transmitted light beam into an intensity modulated beam. A photodetector is configured to detect the intensity modulated beam and generate a photodetector signal. A dual demodulator is coupled to the photodetector and is configured to demodulate the photodetector signal.

19 Claims, 4 Drawing Sheets

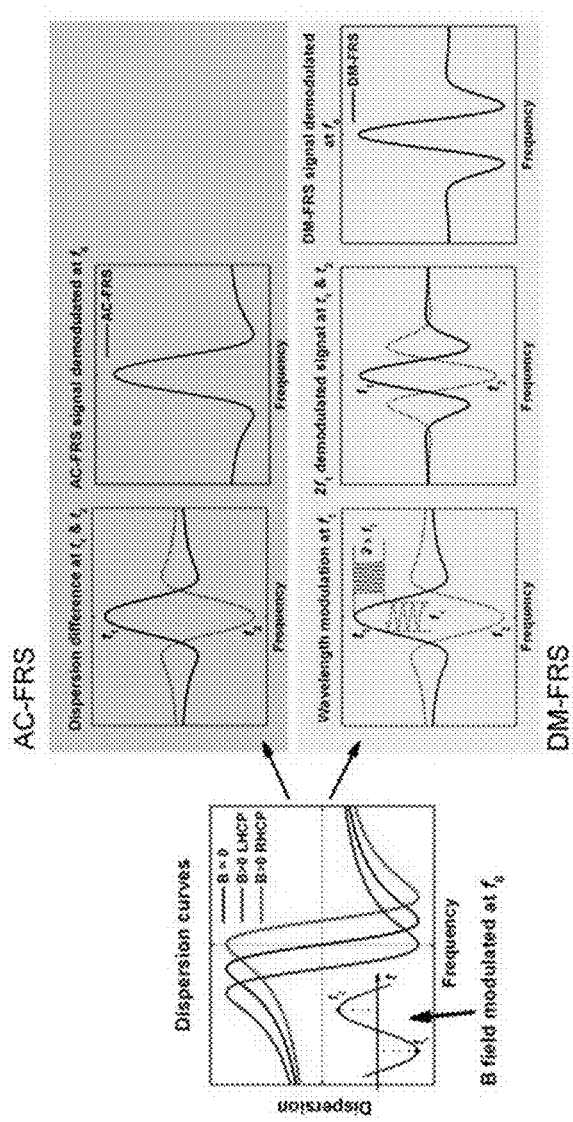
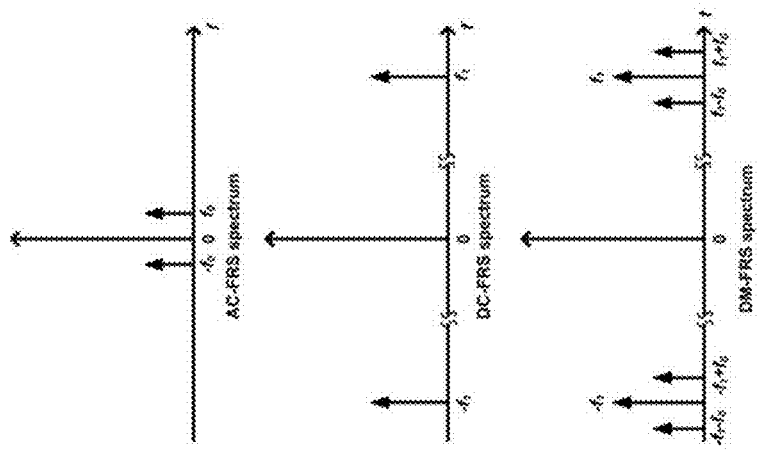
Figure 2a
Figure 2b

DUAL-MODULATION FARADAY ROTATION SPECTROSCOPY

CROSS-REFERENCE TO PRIOR FILED APPLICATIONS

This application claims priority to U.S. provisional application 61/787,851 filed on Mar. 15, 2013 which is incorporated herein in its entirety.

STATEMENT REGARDING FEDERALLY SPONSORED RESEARCH OR DEVELOPMENT

This invention was made with government support under Grant #1R21RR026231. awarded by the National Institutes of Health. The government has certain rights in this invention.

FIELD OF THE INVENTION

The present disclosure generally relates to Faraday rotation spectroscopic (FRS) sensing and in more particular to FRS sensing systems and methods using dual modulation techniques.

BACKGROUND

Faraday rotation is a Magneto-optical phenomenon. This is an interaction between light and a magnetic field that is applied to a medium or sample through which the light passes. The Faraday effect causes a rotation of the plane of polarization of the light source. A conventional Faraday rotation spectroscopic (FRS) system includes a polarized light source and an absorption cell. An AC magnetic modulation field is applied to the sample parallel to the laser-beam direction. If a paramagnetic sample (such as NO molecule, for instance) is present inside the sample chamber, the applied magnetic field rotates the polarization of light source due to the Faraday effect, and the amount of polarization rotation is related to spectroscopic sample parameters, concentration of target species and optical path-length.

Faraday rotation spectroscopy (FRS) has drawn much attention recently because it can provide ultra-sensitive and selective detection of paramagnetic species in gas phase (e.g. NO, NO2, O2). There are two main approaches to perform generation and detection of Faraday rotation signals: (i) AC modulated magnetic field is used to modulate the magneto-optical properties of the sample and a non-modulated laser is used to optically detect the FRS signal (AC-FRS), and (ii) A static (DC) magnetic field is used to interact with the sample gas and a wavelength-modulated laser is used to optically detect the FRS signal (DC-FRS). The major drawback of DC-FRS is that its sensitivity is usually limited by parasitic Fabry-Perot interference fringes generated by multiple optical paths between the laser source and photo detector.

To suppress these effects a balanced photodetection can be employed for DC-FRS measurement. This however requires two well matched photodetectors that are costly and difficult to obtain in the mid-infrared spectral region. In contrast, the signal in AC-FRS can be effectively distinguished from those parasitic effects even if single detector element is used. This is possible, because the modulated magnetic field allows for selective modulation of the magneto-optic properties of the sample and the unwanted magnetically inactive background is suppressed. Therefore in AC-FRS the total system noise consists primarily of photo detection system noise and laser noise, thus it can provide higher sensitivity than DC-FRS. In both AC- and DC-FRS the applied modulation process results in modulated polarization of the transmitted laser beam, which is then detected using a polarizer (analyzer) followed by a photodetector. In order to reject a broadband noise, a phase-sensitive lock-in amplifier is used to demodulate the signal specifically at the modulation frequency or its harmonics.

One important problem that occurs in AC-FRS is related to electro-magnetic interference (EMI) that leads to substantial signal offsets measured by the lock-in amplifier. The EMI occurs due to relatively high currents that are needed to produce required magnetic field by the electromagnetic solenoids. The EMI pick-up is difficult to control and typically occurs in the detector circuitry or laser driving electronics. This significantly deteriorates the system sensitivity and most importantly impacts the system long-term stability, because the amplitude of the pick-up tends to drift over time. Another important problem in AC-FRS is a difficulty of achieving high modulation frequencies with electromagnetic solenoids. driven by high currents Thus the AC-FRS measurements are typically performed at frequencies of several kHz. This low frequency range is dominated by large relative intensity noise (RIN) of laser sources (RIN shows 1/f dependence), and the sensitivity of current AC-FRS systems is strongly limited by RIN. Improved FRS systems and methods are desirable.

SUMMARY OF THE INVENTION

A dual-modulation Faraday rotation spectroscopic (FRS) system is disclosed. The FRS system uses an FRS sample cell configured to subject a sample to a low frequency modulated magnetic field. The system includes a polarized laser light source configured to generate a high frequency wavelength-modulated light beam incident on the sample, the high frequency wavelength-modulated light beam being modulated at a higher frequency than the low frequency modulated magnetic field. A polarizer is configured to receive from the sample a transmitted light beam having a modulated polarization having a polarization rotation and translate the modulated polarization of the transmitted light beam into an intensity modulated beam. A photodetector is configured to detect the intensity modulated beam and generate a photodetector signal. A dual demodulator is coupled to the photodetector and is configured to demodulate the photodetector signal. The high frequency wavelength-modulated light, beam may be wavelength-modulated at a frequency above 10 kHz and the low frequency modulated magnetic field may be modulated at a frequency below 10 kHz. The dual demodulator may be configured to generate a signal proportional to the polarization rotation caused by the sample.

The high frequency wavelength-modulated light beam may be wavelength-modulated at a frequency $f_1$ and the low frequency modulated magnetic field may be modulated at a frequency $f_0$ and the dual demodulator has a high frequency portion configured to demodulate at $f_1$ and a low frequency portion configured to demodulate at $f_0$. A plurality of high frequency wavelength-modulated polarized laser light sources may be provided each being modulated at a different frequency. The plurality of high frequency wavelength-modulated polarized laser light sources may each generate a high frequency wavelength-modulated polarized light, beam modulated at a different frequency. A first optical beam combiner may be used to combine the plurality of high frequency wavelength-modulated polarized laser light beams before the FRS sample cell. A plurality of dual demodulators may be coupled to the photodetector and being configured to demodulate the photodetector signal at multiple frequencies.

The polarizer may be configured to receive the transmitted light beam from the sample and generate an ordinary beam and an extraordinary beam, the system may also include a reference cell configured to perform wavelength modulation spectroscopy on the extraordinary beam and generate an error signal. The high frequency wavelength-modulated polarized laser light source has a wavelength and the system may also include an active feedback loop configured to control the wavelength based on the error signal.

A method of performing dual-modulation Faraday rotation spectroscopic (FRS) sensing is also disclosed. The method use an FRS sample cell configured to subject a sample to a low frequency modulated magnetic field. The method incudes generating a polarized high frequency wavelength-modulated light beam incident on the sample, the high frequency wavelength-modulated light beam being modulated at a higher frequency than the low frequency modulated magnetic field. The polarization of the light beam transmitted through the sample is rotated and the transmitted light beam is translated into an intensity modulated beam. The intensity modulated beam is detected and demodulated. The high frequency wavelength-modulated light, beam may be wavelength-modulated at a frequency above 10 kHz and the low frequency modulated magnetic field may be modulated at a frequency below 10 kHz. A signal proportional to a Faraday polarization rotation caused by the sample may be generated.

The high frequency wavelength-modulated light beam may be modulated at a frequency $f_1$ and the low frequency modulated magnetic field may be modulated at a frequency $f_0$ and the intensity modulated beam is demodulated at $f_1$ and at $f_0$. A plurality of high frequency wavelength-modulated polarized light beams may be generated, each being wavelength-modulated at a different frequency. The plurality of high frequency wavelength-modulated polarized laser light beams may be combined before the FRS sample cell. The multiple FRS signals originating from the plurality of high frequency wavelength-modulated polarized laser light beams transmitted through the sample may be demodulated.

The transmitted light beam from the sample may be used to generate an ordinary beam and an extraordinary beam. A reference cell may be provided for performing wavelength modulation spectroscopy on the extraordinary beam to generate an error signal. The high frequency wavelength-modulated polarized laser light beam has a wavelength and active feedback may be used to control the wavelength based on the error signal.

BRIEF DESCRIPTION OF THE FIGURES

FIG. 2a is a graph showing generation of the dual-modulation (DM)-FRS signal from the Zeeman-split dispersion line using a two-stage modulation/demodulation process, a process of a conventional AC-FRS signal generation is shown for comparison;

FIG. 2b is a graph showing the Frequency spectra of the AC-, DC-, and DM-FRS signals;

DETAILED DESCRIPTION

Figure 1:
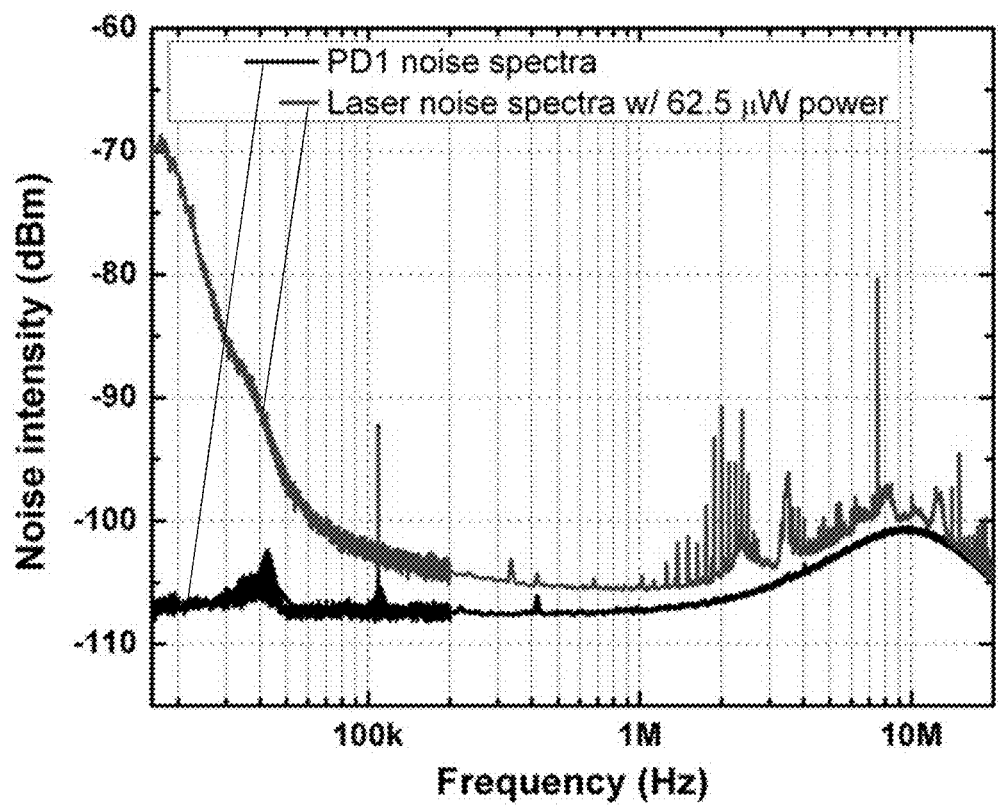
FIG. 1 is a graph showing the spectral distribution of quantum cascade laser intensity noise with a 1/f trend. The photodetector noise spectral distribution is also shown for reference.

Disclosed herein is a new Faraday rotation spectroscopic (FRS) sensing device and method. It is important to realize that the shortcomings of the conventional FRS approaches (both AC-FRS using modulated magnetic field and DC-FRS using static magnetic field) are strongly related to the process of signal demodulation that occurs exactly at the first or higher harmonics of the applied modulation. This causes unwanted EMI-generated background in AC-FRS or residual signals due to sample absorption or parasitic optical interference fringes in DC-FRS. FIG. 1 is a graph showing the spectral distribution of quantum cascade laser intensity noise with a 1/f trend. The photodetector noise spectral distribution is also shown for reference. Thus low frequency modulation of the magnetic field in AC-FRS makes it difficult to achieve shot noise limited operation unless high-stability laser drivers and cryogenically cooled detectors are used to lower the technical noise in this low frequency range. In an attempt of suppression of these unwanted effects signal detection at high frequencies (>10 kHz) FRS is required to achieve sensitivities dominated by the fundamental quantum noise without the need for custom laser drivers (for reduction of laser noise) or cryogenic cooling (for reduction of thermal detector noise). The noise and parasitic effects can be efficiently suppressed through application of dual modulation process that consists of: 1) magnetic field modulation occurs at $f_0$ while 2) the laser wavelength is modulated at the frequency $f_1$ that is much higher than $f_0$ (e.g. for $f_0$ in the single kHz range, $f_1$ is selected in the tens to hundreds of kHz range). Within an instant $\tau$ (assuming $1/f_1 < \tau << 1/f_0$) the FRS signal can be essentially analyzed using a static magnetic field approximation (similar to DC-FRS), which can be demodulated at harmonics of $f_1$. Over longer time the magnetic field modulation at $f_0$ will cause the amplitude of the FRS signal at $f_1$ to oscillate. Thus the photodetector signal contains different harmonics of the carrier frequency $f_1$ with the amplitude modulation (AM) sidebands separated by $f_0$. The detection of the DM-FRS signal. can be performed through a straightforward AM-demodulation at the carrier frequency that corresponds to the desired harmonic of the wavelength modulated FRS signal. FIG. 2a is a graph showing generation of the DM-FRS signal from the Zeeman-split dispersion line using a two-stage modulation/demodulation process, a process of a conventional AC-FRS signal generation is shown for comparison. FIG. 2b is a graph showing the Frequency spectra of the AC-, DC-, and DM-FRS signals.

By applying the disclosed approach to FRS sensing, the system total noise can be effectively suppressed, and the minimum detection limit, to the target trace-gas can be significantly improved as compared to conventional FRS techniques. The disclosed approach also aids in the elimination the unwanted background EMI from the modulated magnetic field so this source of error can be effectively suppressed. This significantly improves long term stability of the system and allows for high accuracy measurements.

By applying the disclosed approach to FRS sensing, multiple lasers can be used to simultaneously generate FRS signals corresponding to different paramagnetic species (e.g. NO, $NO_2$ and their isotopes) in the sample gas mixture. As a result, concentration of multiple paramagnetic species within one sample gas mixture can be determined simultaneously using a single (shared) optical configuration and a single photodetector. This is a significant improvement in cost-efficiency of the instrument.

Figure 3:
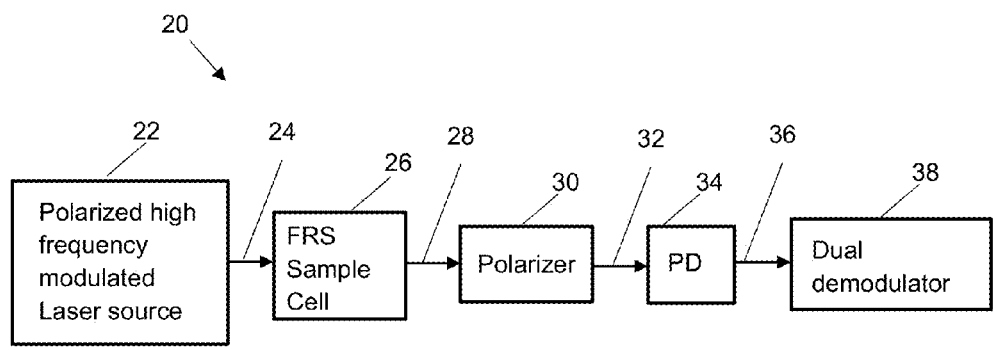
FIG. 3 is a basic block diagram of dual modulation FRS system.

FIG. 3 is a basic block diagram of dual modulation FRS system 20. The system 20 includes a polarized high frequency wavelength-modulated ($f_1$>10 kHz) laser light source 22 having a frequency $f_1$. The term high frequency as user herein refers to frequencies generally above 10 kHz, i.e., $f_1$>10 kHz. It should be understood that a polarized high frequency wavelength-modulated laser light source may be implemented via a variety of methods as is well known in the art. The laser light source 22 directs a polarized high frequency wavelength-modulated light beam 24 into a FRS sample cell 26. It should be understood that the FRS sample cell 26 is subjected to a magnetic field B that is modulated at a low frequency $f_0$. The term low frequency as user herein refers to frequencies generally below 10 kHz, i.e., $f_0$<10 kHz. The resulting Faraday rotated dual modulated light beam 28 exiting the FRS sample cell 26 (transmitted light beam) is directed to a polarizer 30. The transmitted light beam 28 has a modulated polarization and the polarizer 30 translates the modulated polarization of the transmitted light beam into an intensity modulated beam 32. The output of the polarizer 30 (intensity modulated beam 32) is directed to a photodetector 34 for conversion to an electrical photodetector signal 36 which is fed into a dual demodulator 38 for demodulation.

Figure 4:
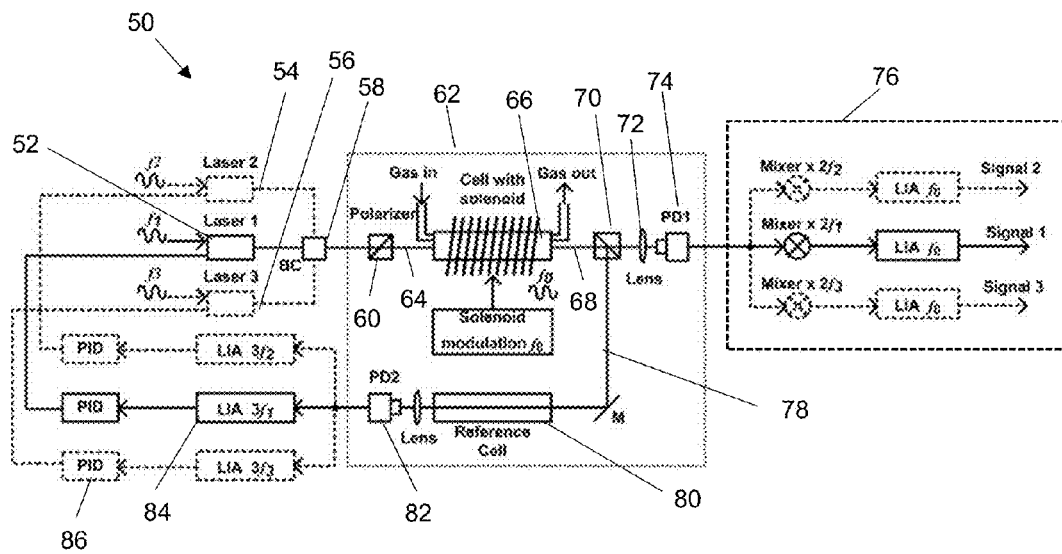
FIG. 4 is a block diagram of a dual modulation FRS system with multiple wavelength light sources.

FIG. 4 is a block diagram of a dual modulation FRS system with multiple wavelength light sources 50. This configuration may be used to monitor three different paramagnetic species. The emitting wavelength of each laser 52, 54, 56 is tuned to coincide with a unique transition line of the target paramagnetic species. The laser beams are combined into a single beam using beam splitters, optical gratings or any other optical beam combiners as shown generally by reference number 58. The combined multi-color laser beam is directed through the optical system shown generally by reference number 62. In this example, the optical system contains polarizer 60, polarization analyzer 70 and photodetector 74. It should be understood that the polarizer 60 may be associated with the light source as shown generally in FIG. 3.

The optical system also includes FRS cell 66. Since after the beam combiner all laser beams follow the same optical path, for clarity only one laser channel is described here (shown by the solid line). A gas cell or sample cell 66 is placed within a magnetic solenoid, The sample cell is generally located between two nearly crossed polarizers (where the first polarizer may be associated with the light, source). The solenoid is modulated by AC current at frequency $f_0$, which results in modulation of magnetic field inside the cell. A linearly polarized laser beam 64 is incident at the sample cell. In the presence of the target species in the gas sample 66, the modulation of the magnetic field results in a modulated polarization rotation observed in the transmitted laser beam 68. The transmitted light passes through the second polarizer 70 (analyzer) which translates the polarization rotation into intensity modulation. The light may optionally pass through one or more lenses shown generally by reference number 72 before being detected by the photodetector 74. The output of the photodetector 74 (electrical signal) is fed into a dual demodulator 76 for demodulation. It should be understood that the dual demodulator may be implemented by a variety of techniques and is not limited to the specific approach shown in FIG. 4.

In contrast to conventional AC-FRS the approach disclosed herein performs additional modulation of the laser wavelength at carrier frequency $f_1$ that is much higher than $f_0$. For semiconductor lasers this can be achieved by adding a sinusoidal modulation of the laser injection current to the laser bias current. The signal photodetected at the carrier frequency $f_1$ contains spectroscopic information resulting from the gas sample absorption (typical wavelength modulated spectrum) as well as spectroscopic information resulting from sample magnetic circular birefringence (FRS spectrum). The latter is modulated by the magnetic field and occurs as the amplitude modulation sidebands separated by $f_0$ from the carrier frequency $f_1$. This dual modulation scheme (DM-FRS) allows for selective demodulation of the FRS signal. The DM-FRS signal can be demodulated at the fundamental carrier frequency $f_1$ or higher harmonics of $f_1$ ($m \cdot f_1$ where m=1, 2, 3 ... etc.). Conventional amplitude demodulation techniques can be used to measure the DM-FRS signals. For example the DM-FRS signal can be demodulated using frequency mixer (frequency down-converter) and lock-in amplifier (that performs noise filtering and signal recovery) as schematically shown by the dual demodulator 76 in FIG. 4. An important advantage enabled by the DM-FRS results from the measurement of the signal around relatively high carrier frequency $m \cdot f_1$, which is much larger than $f_0$. Some advantages of the disclosed approach include: (i) efficient rejection of the EMI at magnetic modulation frequency $f_0$, and (ii) laser RIN that has 1/f spectral distribution is suppressed at high frequencies ($mf_1 \gg f_0$). Thus the DM-FRS system can provide higher sensitivity than conventional AC-FRS, while inheriting all capabilities of AC-FRS (including all its advantages over DC-FRS).

FIG. 4 also includes some additional. circuitry that provides optional functionality. As an example application a continuous monitoring of concentration of paramagnetic species can be performed using DM-FRS. The peak of a DM-FRS signal demodulated using the second harmonic of the carrier ($2f_1$) is proportional to sample concentration and can be used for direct monitoring of molecular concentration. This peak coincides with the absorption line-center and continuous concentration monitoring can be performed after laser frequency is locked to the transition peak. Since DM-FRS uses laser wavelength modulation, the extraordinary beam output from the analyzer allows for convenient control of the laser wavelength by applying standard line-locking techniques. The extraordinary beam 78 is directed through a reference cell SO filled with high concentration of the target species, and a second photodetector 82 is used to perform simple wavelength modulation spectroscopy (WMS). In this configuration the third harmonic WMS signal demodulated with a lock-in amplifier 84 provides an error signal that exhibits a zero-crossing at the center of the target transition. An active feedback loop uses this error signal to control the laser DC bias current and locks the laser wavelength to the absorption line center. This is shown generally by (shown as proportional-integral-derivative (PID) controller 86. This enables continuous monitoring of the DM-FRS signal demodulated at $2f_1$ carrier. In contrast to the "Zeeman modulation" line-locking scheme used in AC-FRS systems reported in the literature, the DM-FRS provides laser frequency control with significantly reduced system complexity and lower power consumption (no additional electromagnetic coils are needed for generation of magnetic fields).

In a multi-laser platform in order to distinguish different laser signals on the photodetector each laser is modulated at different carrier frequencies (e.g. $f_1, f_2, f_3 \ldots$). Thus signals originating from different species can be demodulated independently at different carrier frequencies. Technically this is performed by using a set of frequency mixers and lock-in amplifiers as shown in FIG. 4. Both DM-FRS signal demodulation as well as WMS reference signal detection for active line-locking are performed simultaneously and without cross-talk.

While technological barriers associated with optical components used for DM-FRS fabrication may limit the wavelength coverage of the system, in a multi-laser DM-FRS system targeting multiple chemicals, all shared optical components preferably are able to work within the spectral range that covers all target transition lines. For example, while there are no known commercially available optical components and photodetectors that can work simultaneously at 763 nm and 5.3 μm, when they become available, a DM-FRS system that could simultaneously target detection of $O_2$ at 763 nm and NO at 5.3 μm should be able to be constructed.

Two out of three potential applications (utility A and B) were verified experimentally. Continuous wave (CW) distributed feedback quantum cascade laser (DFB-QCL) operating at 5.2 μm that gives access to the fundamental ro-vibrational transitions of nitric oxide (NO). Within the available laser tuning range the NO R(8.5)e transition at 1906.14 $cm^{-1}$ has been selected as the test target line. Two $MgF_2$ Rochon prisms were used as the polarizer and the analyzer in the system. The beam was directed into a 15 cm gas cell surrounded by a solenoid generating ~100 Gauss AC magnetic field modulated at frequency of $f_0$=3.26 kHz. A calibrated gas mixture with 2 ppm-v NO in dry $N_2$ was used as a sample gas for system characterization. The NO concentration in the reference cell was adjusted to provide strong WMS signal for line-locking. The pressure inside both cells was set to 30 Torr. Two TE-cooled MCT photo detectors were used: one for DM-FRS signal detection, and one for WMS line-locking.

To perform test against well-established AC-FRS technology we have tested both measurement techniques (AC-FRS and the new DM-FRS) using the same optical setup. For performance comparison a minimum detectible polarization rotation angle $\theta_{min_{FRS}}$ was used. This parameter is considered a reliable figure of merit (FOM) for FRS systems. Assuming the system works at the optimum analyzer offset based on basic system parameters such as: detector noise, laser power, and laser noise. This can be expressed by:

$$\Theta_{min_{FRS}} = \sqrt{\frac{\Delta f \cdot NEP(\omega_m) \cdot \sigma(\omega_m)}{2P_o}}$$

Where $\Delta f$ is the lock-in effective bandwidth, $NEP(\omega_m)$ and $\sigma(\omega_m)$ are photo detector NEP and laser source RIN at the signal frequency $\omega_m$, respectively. $P_0$ is the optical power before the polarization analyzer. Equation 1 quantitatively shows that the system sensitivity is directly proportional to the product of $\sqrt{NEP(\omega_m) \cdot \sigma(\omega_m)}$.

Figure 5A:
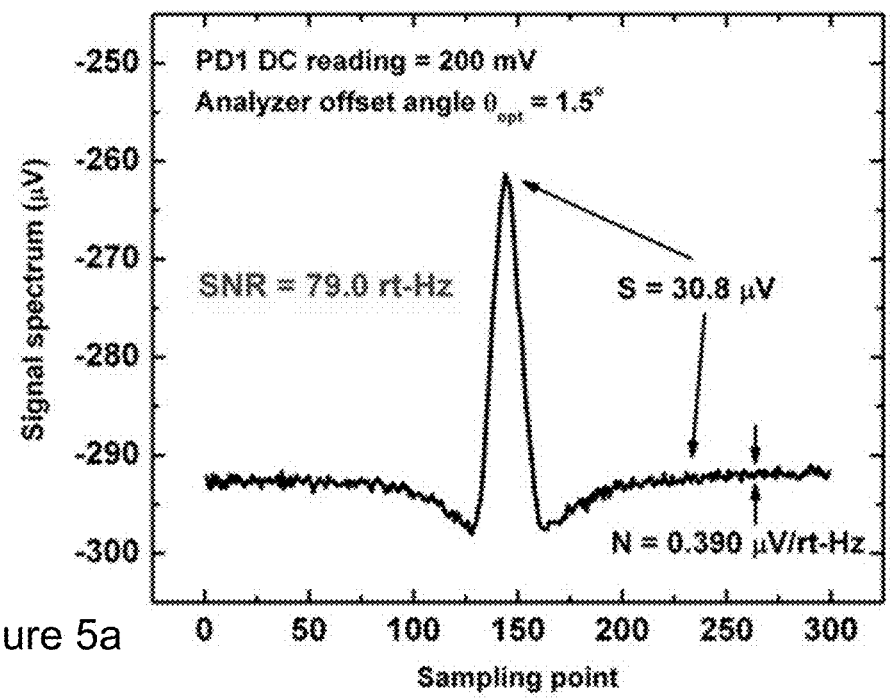
FIG. 5a is a graph of AC-FRS spectra of NO R(8.5)e transition at 1906.14 cm$^{-1}$ acquired at optimized analyzer offset angle $\theta_{opt}=1.5°$.

For conventional AC-FRS the signal frequency is that of magnetic field modulation and is equal to 3.26 kHz in the investigated system. A typical spectrum acquired with conventional AC-FRS set-up is shown in FIG. 5a. The σ and NEP measured at 3.26 kHz are $1.42 \times 10^{-6}$ $Hz^{-1/2}$ and $1.18 \times 10^{-11}$ $W/Hz^{1/2}$, respectively. The optimized analyzer offset angle of ~1.5° was found for this AC-FRS system. The minimum detection limit (MDL) to nitric oxide concentration achieved with this system was ~25.3 ppb-v/$Hz^{1/2}$, and a minimum detectible polarization rotation angle is $\theta_{min_{FRS}}=2.64\times 10^{-8}$ rad/$Hz^{1/2}$. It should be noted that the spectrum in FIG. 5a exhibits a baseline offset of ~291 μV, which is almost 10 times the strength of signal at the peak. This is an influence of the EMI pick-up in the detection system, which can vary in time and strongly limits long-term stability of the AC-FRS systems.

Figure 5B:
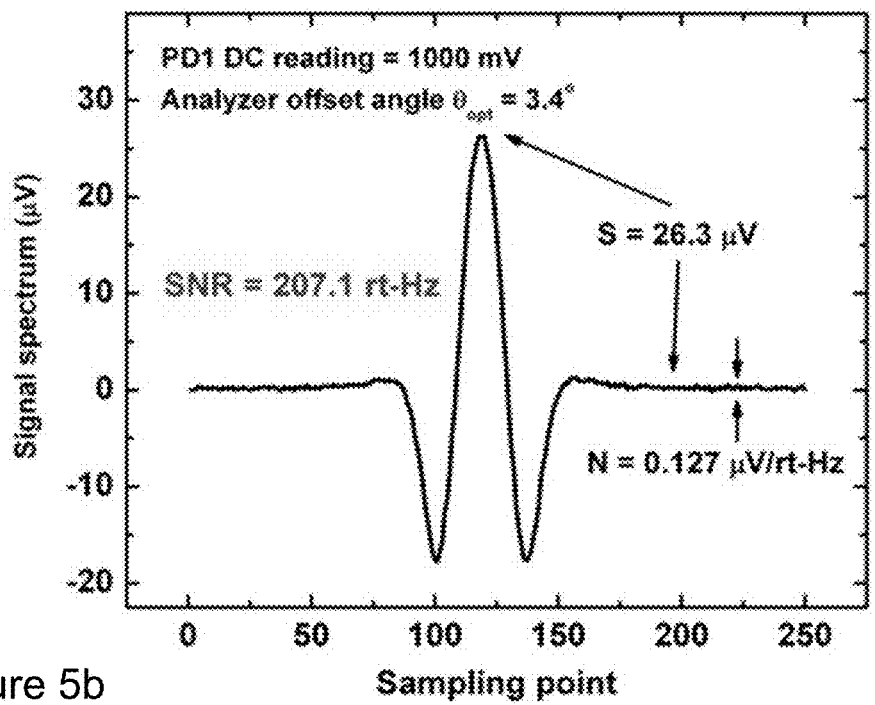
FIG. 5b is a graph of DM-FRS spectra of NO R(8.5)e transition at 1:906.14 cm$^{-1}$ acquired at optimized analyzer offset angle $\theta_{opt}=3.4°$.

For comparison FIG. 5b shows the same measurements performed with DM-FRS using exactly the same optical system. The DM-FRS uses wavelength modulation carrier frequency of $f_1$=50 kHz (currently limited by capabilities of a lock-in amplifier used in this study). There are two additional parameters that need to be optimized in order to generate the maximum DM-FRS signal: (a) the modulation depth of the laser current was optimized to match the transition linewidth; (b) the phase of the LO reference for the frequency mixer must be in phase with the measured signal. Since the demodulation is performed at the $2f_1$ carrier the laser RIN and photodetector NEP at 100 kHz must be taken into account for further optimization. In this system the RIN at 100 kHz is 17.8 lower than RIN at 3.26 kHz. NEP at 100 kHz is 3.1 times lower than NEP in low frequency range. Thus the analyzer can be further opened to an optimum analyzer offset angle of ~3.4°. The MDL to nitric oxide concentration achieved with this system was ~9.7 ppb-v/$Hz^{1/2}$, and a minimum detectible polarization rotation angle is $\theta_{min_{FRS}}=3.55\times 10^{-9}$ rad/$Hz^{1/2}$. This is 7.4 times better than AC-FRS system. It should be noted however that while the improved 7.4 times the MDL only improved by a factor of 2.6. This is strictly related to the physics of modulation process, which intrinsically exhibits decrease in the strength of the $2^{nd}$ harmonic FRS signal used in DM-FRS with respect to the $1^{st}$ harmonic used in AC-FRS. If $1^{st}$ harmonic DM-FRS is used the MDL enhancement should be similar to the enhancement of $\theta_{min_{FRS}}$. Most importantly the EMI baseline offset observed in AC-FRS was effectively removed, indicating better long term system performance of DM-FRS. When working in continuous line-locking mode, the normalized MDL is ~6 ppb-v/$Hz^{1/2}$, about ~4 times more sensitive than conventional AC-FRS. The highest MDL of ~1.2 ppb-v/$Hz^{1/2}$ could be achieved when ~1 min averaging is performed.

In the systems constructed to date, the highest wavelength modulation frequency is limited by the available lock-in amplifier. The sensitivity can be further enhanced when high-speed lock-in with higher demodulation frequency is employed. Multi-species measurement with multiple QCLs may be accomplished with appropriate laser sources. The disclosed approach can provide improved the system sensitivity, reduced the complexity and long term stability compared to conventional FRS technique. Existing AC-FRS systems can be easily converted to operate using the disclosed approach.

The disclosed approach can be applied when concentration of multiple paramagnetic species needs to be measured (e.g. atmosphere $NO_x$ ($NO+NO_2$) measurement, or measurement of isotopic ratio of any paramagnetic species). With dual-modulation FRS concentration of several paramagnetic species can be retrieved using a single optical configuration and photo detector. This will largely reduce the cost to build multiple sensors with each of them targeting an individual gas species.

The disclosed process and device has utility for, among others, manufacturers of laser equipment and laser sensor systems, manufacturers of $NO_x$ analyzers, companies developing systems for automobile and/or industrial emission control, and manufacturers of sensors for environmental or air quality applications.

The following references are part of the application and are incorporated by reference in their entirety as if fully set forth herein:

[1] Lewicki, R., Doty, J. H., Curl, R. F., Tittel, F. K., and Wysocki, G., "Ultrasensitive detection of nitric oxide at 5.33 mu m by using external cavity quantum cascade laser-based Faraday rotation spectroscopy," Proceedings of the National Academy of Sciences of the United States of America, 106 (31), 12587-12592 (2009).

[2] Y. Wang, M. Nikodem, and G. Wysocki, "Cryogen-free heterodyne-enhanced mid-infrared Faraday rotation spectrometer," Opt. Expr. 21, 740-755 (2013).

What is claimed is:

1. A Faraday rotation spectroscopic (FRS) system having an FRS sample cell configured to subject a sample to a low frequency modulated magnetic field, the system comprising:
a polarized laser light source configured to generate a high frequency wavelength-modulated light beam incident on the sample, the high frequency wavelength-modulated light beam being modulated at a higher frequency than the low frequency modulated magnetic field;
a polarizer configured to receive from the sample a transmitted light beam having a modulated polarization and a polarization rotation and translate the modulated polarization of the transmitted light beam into an intensity modulated beam;
a photodetector configured to detect the intensity modulated beam and generate a photodetector signal;
a dual demodulator coupled to the photodetector and being configured to demodulate the photodetector signal.

2. The system of claim 1 wherein the high frequency wavelength-modulated light beam is wavelength-modulated at a frequency above 10 kHz and the low frequency modulated magnetic field is modulated at a frequency below 10 kHz.

3. The system of claim 1 wherein the dual demodulator is configured to generate a signal proportional to the polarization rotation caused by the sample.

4. The system of claim 1 wherein the high frequency wavelength-modulated light beam is wavelength-modulated at a frequency $f_1$ and the low frequency modulated magnetic field is modulated at a frequency $f_0$ and the dual demodulator has a high frequency portion configured to demodulate at $f_1$ and a low frequency portion configured to demodulate at $f_0$.

5. The system of claim 1 further comprising a plurality of high frequency wavelength-modulated polarized laser light sources each being modulated at a different frequency.

6. The system of claim 1 further comprising a plurality of high frequency wavelength-modulated polarized laser light sources each generating a high frequency wavelength-modulated polarized light beam modulated at a different frequency.

7. The system of claim 6 further comprising a first optical beam combiner configured to combine the plurality of high frequency wavelength-modulated polarized laser light beams before the FRS sample cell.

8. The system of claim 6 further comprising a plurality of dual demodulators coupled to the photodetector and being configured to demodulate the photodetector signal at multiple frequencies.

9. The system of claim 1 wherein the polarizer is configured to receive the transmitted light beam from the sample and generate an ordinary beam and an extraordinary beam, the system further comprising a reference cell configured to perform wavelength modulation spectroscopy on the extraordinary beam and generate an error signal.

10. The system of claim 9 wherein the polarized laser light source has a wavelength and the system further comprises an active feedback loop configured to control the wavelength based on the error signal.

11. A method of performing Faraday rotation spectroscopic (FRS) sensing using an FRS sample cell configured to subject a sample to a low frequency modulated magnetic field, the method comprising:
generating a polarized high frequency wavelength-modulated light beam incident on the sample, the high frequency wavelength-modulated light beam being modulated at a higher frequency than the low frequency modulated magnetic field;
rotating the polarization of the light beam transmitted through the sample and translating the transmitted light beam into an intensity modulated beam;
detecting the intensity modulated beam; and
demodulating the intensity modulated beam.

12. The method of claim 11 wherein the high frequency wavelength-modulated light beam is modulated at a frequency above 10 kHz and the low frequency modulated magnetic field is modulated at a frequency below 10 kHz.

13. The method of claim 11 further comprising generating a signal proportional to the polarization rotation caused by the sample.

14. The method of claim 11 wherein the high frequency wavelength-modulated light beam is modulated at a frequency $f_1$ and the low frequency modulated magnetic field is modulated at a frequency $f_0$ and the intensity modulated beam is demodulated at $f_1$ and at $f_0$.

15. The method of claim 11 further comprising generating a plurality of high frequency wavelength-modulated polarized light beams each being modulated at a different frequency.

16. The method of claim 15 further comprising combining the plurality of high frequency wavelength-modulated polarized laser light beams before the FRS sample cell.

17. The method of claim 15 further comprising demodulating multiple FRS signals originating from the plurality of high frequency wavelength-modulated polarized laser light beams transmitted through the sample.

18. The method of claim 11 further comprising receiving the transmitted light beam from the sample and generating an ordinary beam and an extraordinary beam, providing a reference cell and performing wavelength modulation spectroscopy on the extraordinary beam and generating an error signal.

19. The method of claim 18 wherein the high frequency wavelength-modulated polarized laser light beam has a wavelength and performing active feedback to control the wavelength based on the error signal.

* * * * *